(12) United States Patent
Kaforey

(10) Patent No.: US 10,842,574 B2
(45) Date of Patent: Nov. 24, 2020

(54) ROBOTIC PATIENT PROTECTION SYSTEM COMPRISING A HEAD MASK STRUCTURE, CONFIGURED TO PROTECT THE HEAD OF A PATIENT, FOR USE IN ROBOTIC SURGICAL PROCEDURES

(71) Applicant: Craig Kaforey, Allison Park, PA (US)

(72) Inventor: Craig Kaforey, Allison Park, PA (US)

(73) Assignee: Xodus Medical, Inc., New Kensington, PA (US)

( * ) Notice: Subject to any disclaimer, the term of this patent is extended or adjusted under 35 U.S.C. 154(b) by 1218 days.

(21) Appl. No.: 14/205,520

(22) Filed: Mar. 12, 2014

(65) Prior Publication Data

US 2015/0181951 A1 Jul. 2, 2015

Related U.S. Application Data

(60) Provisional application No. 61/793,874, filed on Mar. 15, 2013.

(51) Int. Cl.
*A61B 34/30* (2016.01)
*A61G 13/12* (2006.01)
*A61B 46/00* (2016.01)
*A61B 90/00* (2016.01)

(52) U.S. Cl.
CPC .............. *A61B 34/30* (2016.02); *A61B 46/00* (2016.02); *A61B 2090/08021* (2016.02); *A61G 13/121* (2013.01)

(58) Field of Classification Search
CPC ...... A61G 13/12; A61G 13/121; A61B 34/30; A61B 46/00; A61B 2090/08021

USPC .................................. 128/846, 845; 2/9, 410
See application file for complete search history.

(56) References Cited

U.S. PATENT DOCUMENTS

| | | | |
|---|---|---|---|
| 4,122,847 A | 10/1978 | Craig | |
| 4,209,473 A | 6/1980 | Coyne | |
| 4,220,730 A | 9/1980 | Coyne | |
| 4,574,105 A | 3/1986 | Donovan | |
| 4,719,039 A | 1/1988 | Leonardi | |
| 4,877,814 A | 10/1989 | Ito | |
| 5,180,751 A | 1/1993 | Park et al. | |
| 5,206,082 A | 4/1993 | Malone | |
| 5,527,573 A | 6/1996 | Park et al. | |
| 5,567,742 A | 10/1996 | Park | |
| 5,613,501 A * | 3/1997 | Michelson | ............ A61F 5/3707 5/637 |
| 6,112,333 A | 9/2000 | Mazzei | |
| 6,245,266 B1 | 6/2001 | Ramesh et al. | |
| 6,453,476 B1 | 9/2002 | Moore, III | |
| 6,490,737 B1 * | 12/2002 | Mazzei | .................. A61G 13/12 128/846 |
| 6,637,058 B1 | 10/2003 | Lamb | |
| 6,773,796 B1 | 8/2004 | Di Cesare et al. | |
| 6,895,619 B1 | 5/2005 | Lee | |
| 7,078,443 B2 | 7/2006 | Milliren | |

(Continued)

FOREIGN PATENT DOCUMENTS

WO 2013106426 A2 7/2013

*Primary Examiner* — Kari K Rodriquez
*Assistant Examiner* — Caitlin A Carreiro
(74) *Attorney, Agent, or Firm* — The Webb Law Firm

(57) ABSTRACT

A robotic patient protection system and method including a head mask structure, configured to protect the head of a patient, for use in robotic surgical procedures.

16 Claims, 18 Drawing Sheets

(56) References Cited

U.S. PATENT DOCUMENTS

| | | |
|---|---|---|
| 7,360,543 B1 * | 4/2008 | Coleman .............. A61F 5/3769 |
| | | 128/869 |
| 7,426,763 B2 | 9/2008 | Mazzei et al. |
| 7,574,759 B2 | 8/2009 | Wilson et al. |
| 7,748,387 B1 | 7/2010 | Vu et al. |
| 7,759,404 B2 | 7/2010 | Burgun et al. |
| 7,789,461 B2 | 9/2010 | Leeds |
| 7,799,841 B2 | 9/2010 | Stadlbauer et al. |
| 7,850,630 B1 | 12/2010 | Vu et al. |
| 7,984,715 B2 * | 7/2011 | Moyers ................ A61N 5/1049 |
| | | 128/846 |
| 8,001,970 B2 | 8/2011 | King et al. |
| 8,066,524 B2 | 11/2011 | Burbank et al. |
| 8,261,385 B2 | 9/2012 | Mazzei et al. |
| 8,269,825 B1 | 9/2012 | Vu et al. |
| 8,302,213 B2 | 11/2012 | Kriesel |
| 8,359,689 B2 | 1/2013 | Warren et al. |
| 8,399,085 B2 | 3/2013 | Moore, III et al. |
| 8,464,720 B1 | 6/2013 | Pigazzi et al. |
| 8,511,314 B2 | 8/2013 | Pigazzi et al. |
| 8,648,900 B2 | 2/2014 | Vu et al. |
| 2008/0283063 A1 * | 11/2008 | Wilcox .................. A42B 3/28 |
| | | 128/206.17 |
| 2010/0307509 A1 | 12/2010 | King et al. |
| 2011/0253150 A1 | 10/2011 | King et al. |
| 2012/0054966 A1 * | 3/2012 | Bacon ................. A47G 9/1081 |
| | | 5/636 |
| 2012/0297526 A1 * | 11/2012 | Leon ....................... A42B 3/08 |
| | | 2/413 |

\* cited by examiner

US 10,842,574 B2

ROBOTIC PATIENT PROTECTION SYSTEM COMPRISING A HEAD MASK STRUCTURE, CONFIGURED TO PROTECT THE HEAD OF A PATIENT, FOR USE IN ROBOTIC SURGICAL PROCEDURES

CROSS-REFERENCE TO RELATED APPLICATIONS

This application claims the benefit of U.S. Provisional Application No. 61/793,874, having the title "ROBOTIC PATIENT PROTECTION SYSTEM," and filed on Mar. 15, 2013.

BACKGROUND

1. Technical Field

The present application relates to a robotic patient protection system comprising a head mask structure, configured to protect the head of a patient, for use in robotic surgical procedures.

2. Background Information

Robotic operation equipment may be programmed to take a shortest path between a point where an operating instrument is at to a point where the operating instrument is desired to be. A surgeon may make a mistake in moving an operating instrument from a point where the operating instrument is at to a point where the operating instrument is to be. To restrict or minimize the possibility of a patient being injured due to these errors or mistakes made by robotic operation equipment or a surgeon during robotic surgery, a protective face mask configured to cover the face or face area of a patient is desired.

OBJECT OR OBJECTS

An object of the present application may be to provide a patient protection system, comprising at least a mask and a head rest in one possible embodiment, configured to cover the face area of a patient to assist in protecting a patient from injury during robotic surgery.

DESCRIPTION OF EMBODIMENT OR EMBODIMENTS

Figure 1:
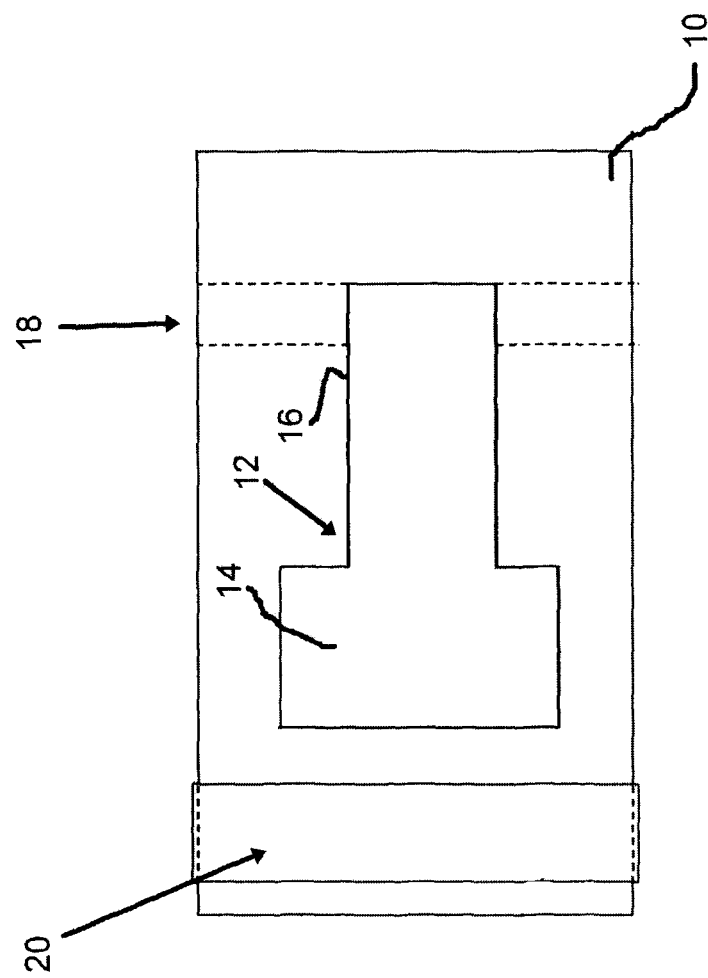
FIG. 1 shows a top view of one possible embodiment of a face unit of a patient protection system according to one possible embodiment of the present application.

As shown in FIG. 1, in version 1 of a face unit 10, the face mask 10 may comprise a body 12 made from plastic foam material, which can possibly be deformed upon impact by an operating instrument. The body 12 of the face mask 10 may also be somewhat deformed by the face of a patient to form a reasonably comfortable fit between the face of the patient and the face mask 10. In one possible embodiment of the present application, the mask 10 may comprise a plastic plate protecting layer, made from hard plastic, which may protect the body 12 of the mask 10 and a patient from moderate to severe impact with an operating instrument or other parts of the movable arms of the robotic operating system. The body 12 of the mask 10 may be made of for example a polyethylene foam or alternatively of a polypropylene foam. In order for operating room personnel to be able to observe the eyes of a patient during an operation, an opening 14 is provided in the body 12 of the mask 10. Further, in order for operating room personnel to be able to observe the intubation in the mouth of a patient during an operation, an opening 16 is provided in the body 12 of the mask 10. As shown in FIG. 1, the opening 16 extends from the opening 14. The opening 18 for an intubation tube or notch 18 for an intubation tube is provided, shown in dotted lines in FIG. 1. A strap 20 configured to hold the face mask 10 to a patient is also provided.

Figure 2:
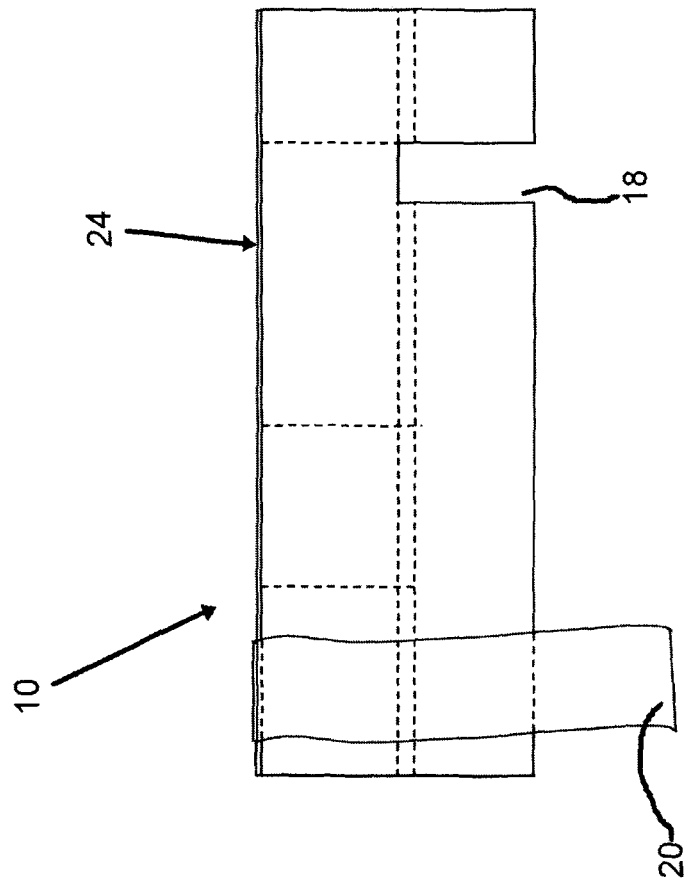
FIG. 2 shows a side view of the face unit of the possible embodiment of a patient protection system as shown in FIG. 1.

As shown in FIG. 2, an opening 18, which permits the intubation equipment to pass through the mask 10, is provided. A strap 20 is connected to the mask 10 in order to hold the mask in place on a patient. A plastic plate protecting layer 24, made from hard plastic which may protect the body 12 of the mask 10 from moderate or severe impact with an operating instrument or other parts of the movable arms of the robotic operating system, is also shown in FIG. 2. Alternatively, metal such as aluminum or another material such as a ceramic, could be used as the protecting layer 24.

Figure 3:
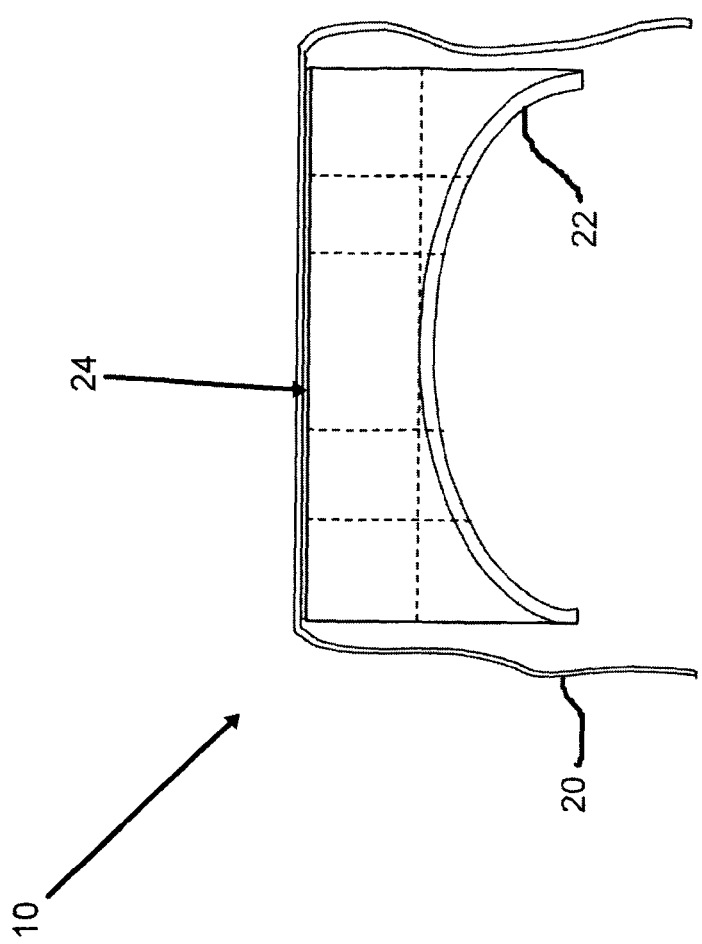
FIG. 3 shows an end view of the face unit of the possible embodiment of a patient protection system as shown in FIG. 1.

As shown in FIG. 3, a layer of viscoelastic foam 22 is attached to the body 12 of the mask 10 and is configured to contact the face of a patient during use. The viscoelastic foam 22 may generally conform to the face of a patient in order to distribute the load of the mask 10 over the face of a patient in a relatively comfortable manner. The plastic plate protecting layer 24 is also shown.

The plastic layer may be made from a number of hard plastic materials, such as those used for hockey masks, such as, for example, fiberglass, Kevlar, thermoplastic composites, or thermoset composites.

In the possible embodiment of the present application as shown in the figures, the body of the mask 10 may be about twelve inches long and about ten inches wide. The opening 14 may be about two and a half inches long and about five and a half inches wide. The opening 16 may be about three and a half inches long and about three inches wide. The opening 18 for an intubation tube may be about one inch long and span the width of the face mask 10. The opening 16 may be disposed about two inches from the bottom side of the face mask 10. The opening 14 may be disposed about four inches from the top side of the face mask 10. The measurements given in this paragraph are for one possible embodiment of the present application. Measurements of other possible embodiments may be greater or lesser than the values disclosed above.

Figure 4:
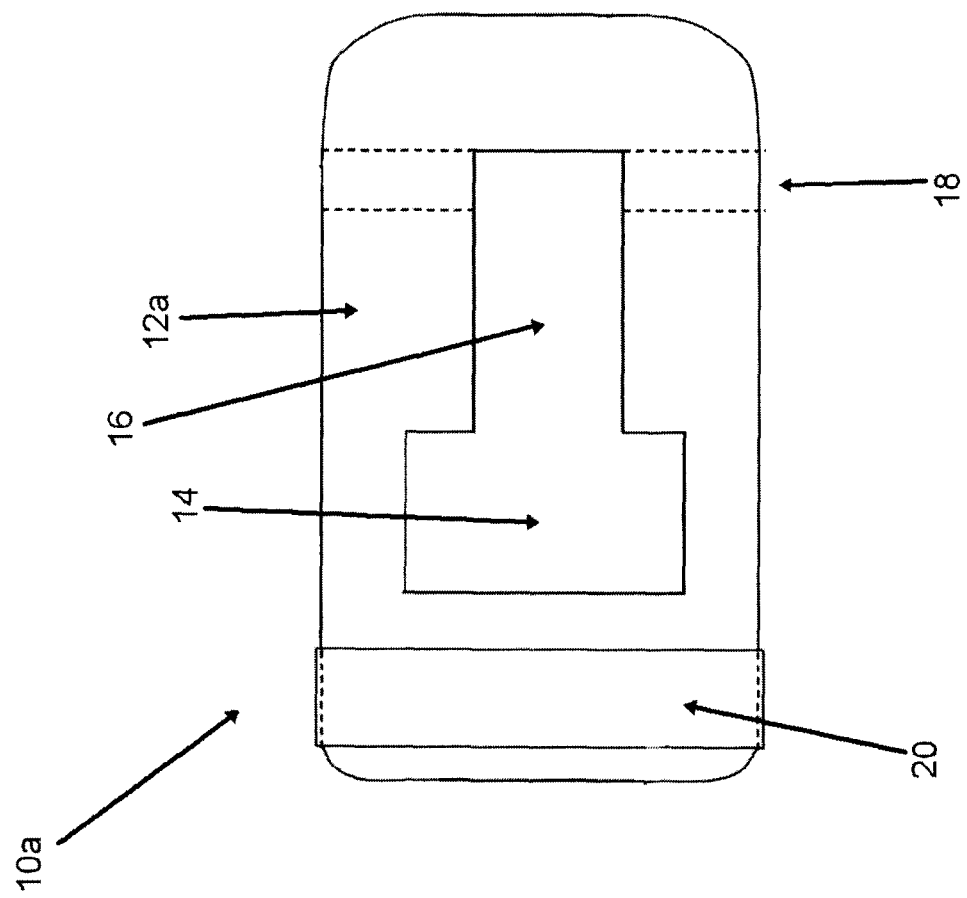
FIG. 4 shows a top view of another possible embodiment of a face unit of a patient protection system according to one possible embodiment of the present application.

FIG. 4 shows an alternative embodiment of a face mask 10a according to the present application, in which the corners of the face mask are curved. The face mask 10a comprises a body 12a of foam which is rounded at the corners. The face mask 10a also comprises the opening 14, the opening 16, the notch 18 for an intubation tube, and the strap 20.

Figure 5:
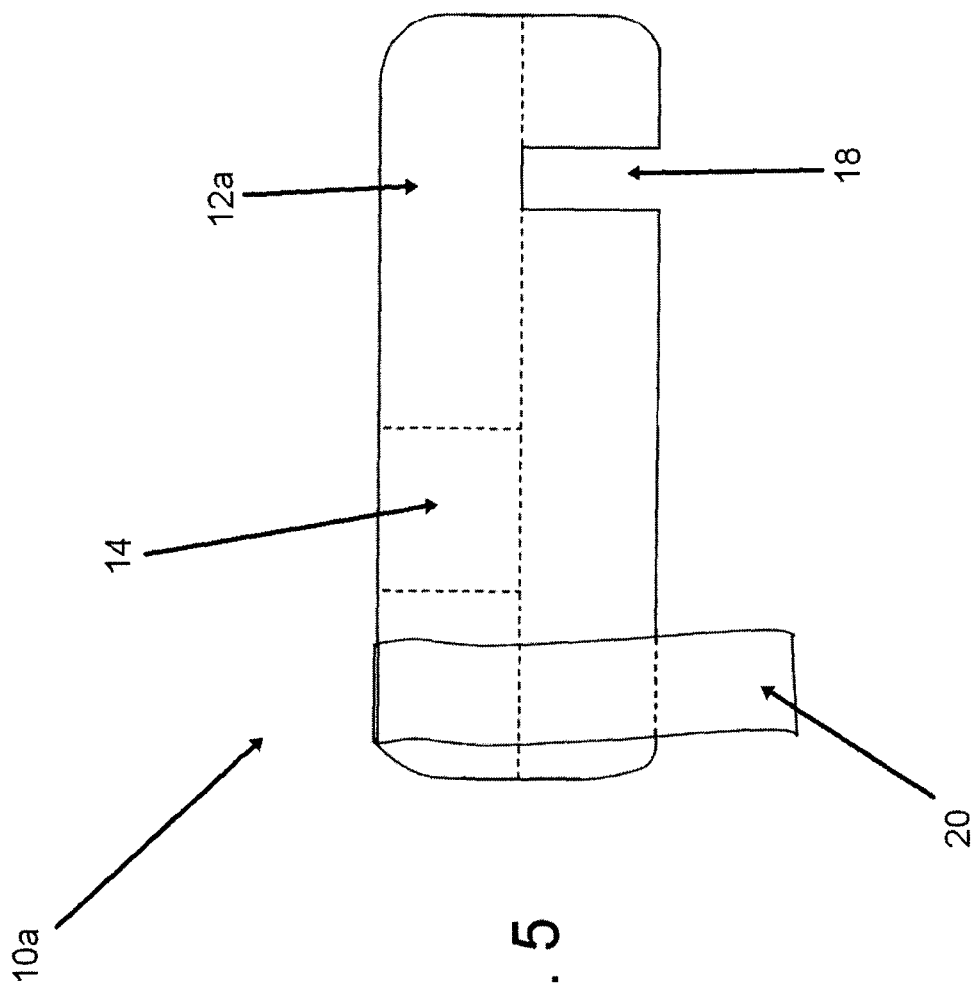
FIG. 5 shows a side view of the face unit of the possible embodiment of a patient protection system as shown in FIG. 4.

FIG. 5 shows the alternative embodiment of the face mask 10a of FIG. 4 from the side. The face mask 10a comprises the body 12a, the opening 14, the notch 18 for an intubation tube, and the strap 20. In yet another alternative embodiment of the present application, the strap 20 could be replaced with other means for connecting the face unit 10 to the head rest unit 90 such as screws and threaded holes or unthreaded holes or the like such as spring connectors that engage a tang.

In yet a further alternative embodiment of the present application, the patient could be lying face down on the medical procedure table. The back of the head would then be up, and therefore the hard covering portion of the mask would be disposed on the portion of the patient protection system facing upward, which would be above the back portion of the patient's head.

In yet another alternative embodiment of the present application, the side of the head could be covered by the part of the patient protection system facing upward.

Figure 6:
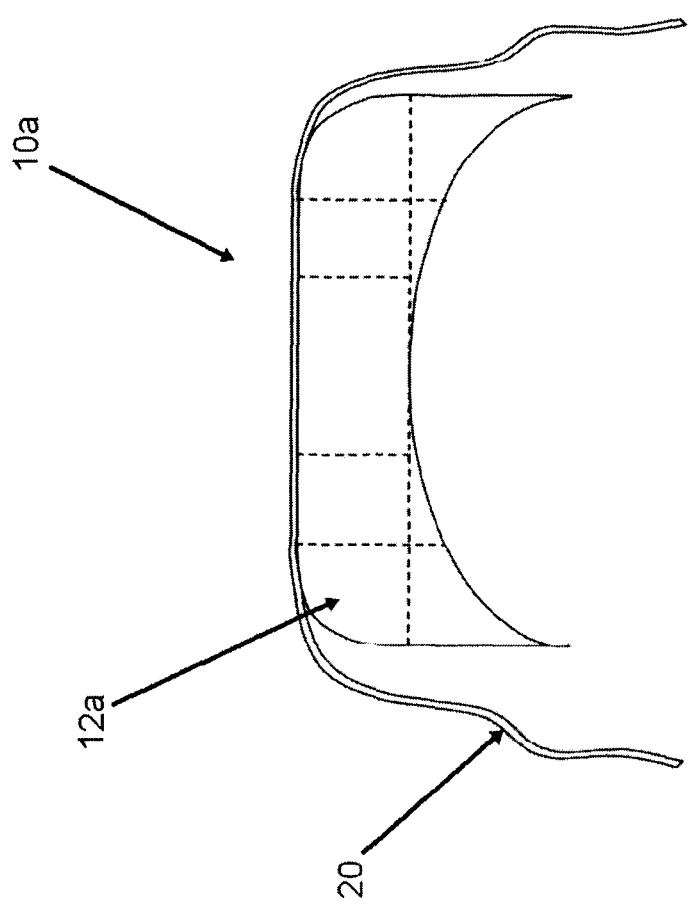
FIG. 6 shows an end view of the face unit of the possible embodiment of a patient protection system as shown in FIG. 4.

FIG. 6 shows the face mask 10a of FIGS. 4 and 5 from an end of the mask 10a, but without viscoelastic material on the inside thereof. The mask 10a comprises the body 12a and the strap 20.

Figure 7:
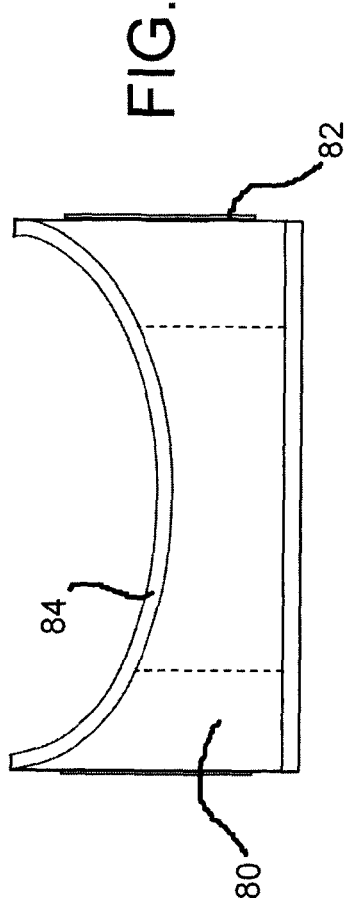
FIG. 7 shows an end view of one possible embodiment of a head rest unit of a patient protection system according to one possible embodiment of the present application.

As shown in FIG. 7, the patient protection system may also comprise a head rest as well as a face mask. One possible embodiment of a head rest is shown in FIG. 7. As shown in FIG. 7, the strap 20 of a face mask of the present application is connectable to a head rest 80. A Velcro hook and loop arrangement 82 is shown on the sides of the head rest 80 to which the straps 20, which also comprise a hook and loop arrangement, can be attached. In at least one possible embodiment of the present application, the head rest 80 may comprise a plastic plate protecting layer. Also shown in FIG. 7 is a layer 84 of viscoelastic foam. The layer 84 of the head rest 80 may be configured to contact the back of a patient's head in order to provide a somewhat comfortable head rest for a patient.

Figure 8:
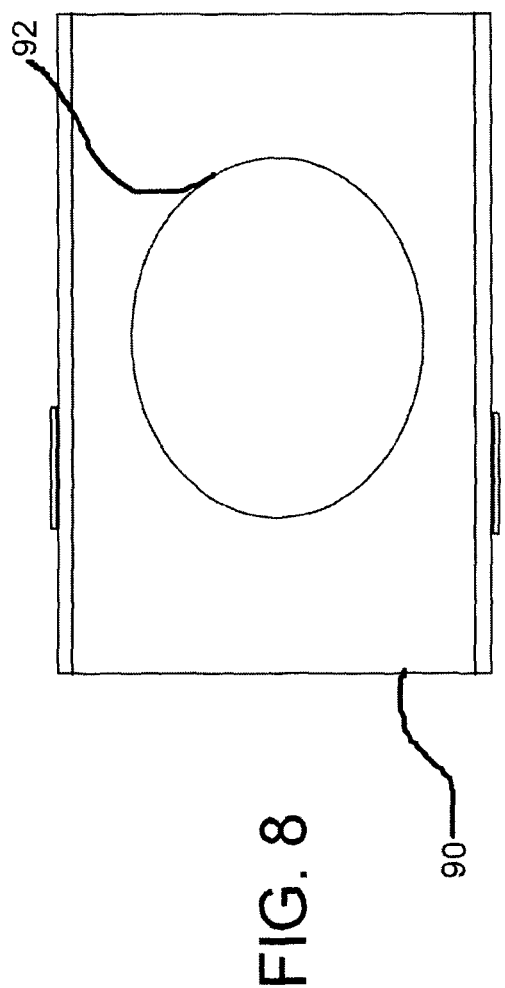
FIG. 8 shows a top view of the head rest unit of the possible embodiment of a patient protection system as shown in FIG. 7.
Figure 9:
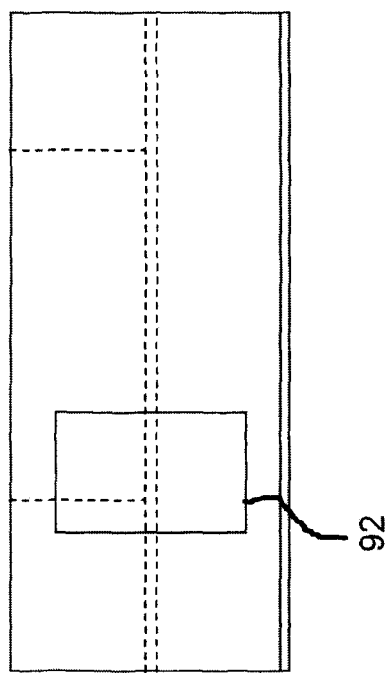
FIG. 9 shows a side view of the head rest unit of the possible embodiment of a patient protection system as shown in FIG. 7.

FIG. 8 shows a headrest unit 90 with a hollowed out area 92 into which the back of the head of the patient can be disposed. This hollowed out area 92 is in one embodiment also lined with a viscoelastic material foam which conforms substantially to the head of patient to cradle the back of the head as comfortably as possible. FIG. 9 shows a side view of the headrest 90 with the Velcro strap receiving member 92 disposed thereon. In at least one possible embodiment of the present application, the head rest 90 may not comprise a hole, and may substantially comprise viscoelastic foam.

FIG. 9 shows a side view of one possible embodiment of a head rest unit of a patient protection system according to the present application.

Figure 10:
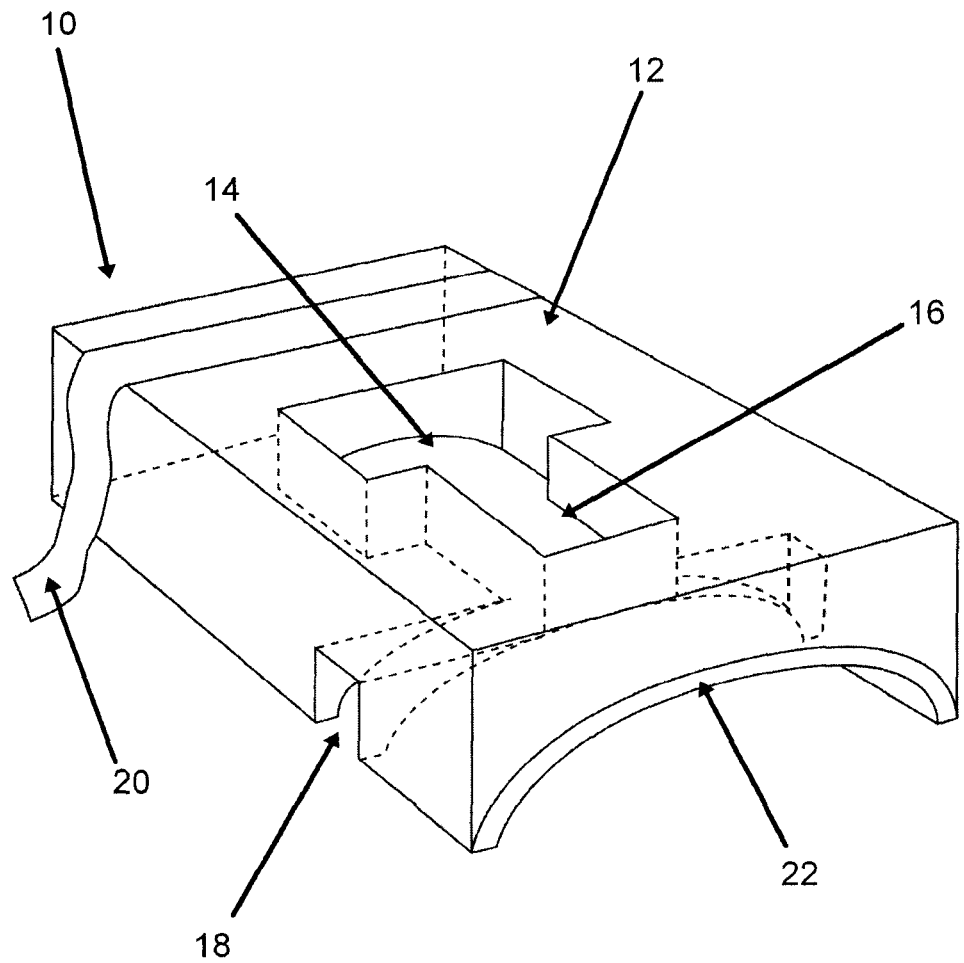
FIG. 10 is a perspective view of the possible embodiment as shown in FIGS. 1-3.

FIG. 10 is a perspective view of the possible embodiment of the face mask 10 as shown in FIGS. 1-3. The face mask 10 comprises the body 12, the opening 14, the opening 16, the notch 18 for an intubation tube, the strap 20, and the viscoelastic inner layer 22.

Figure 11:
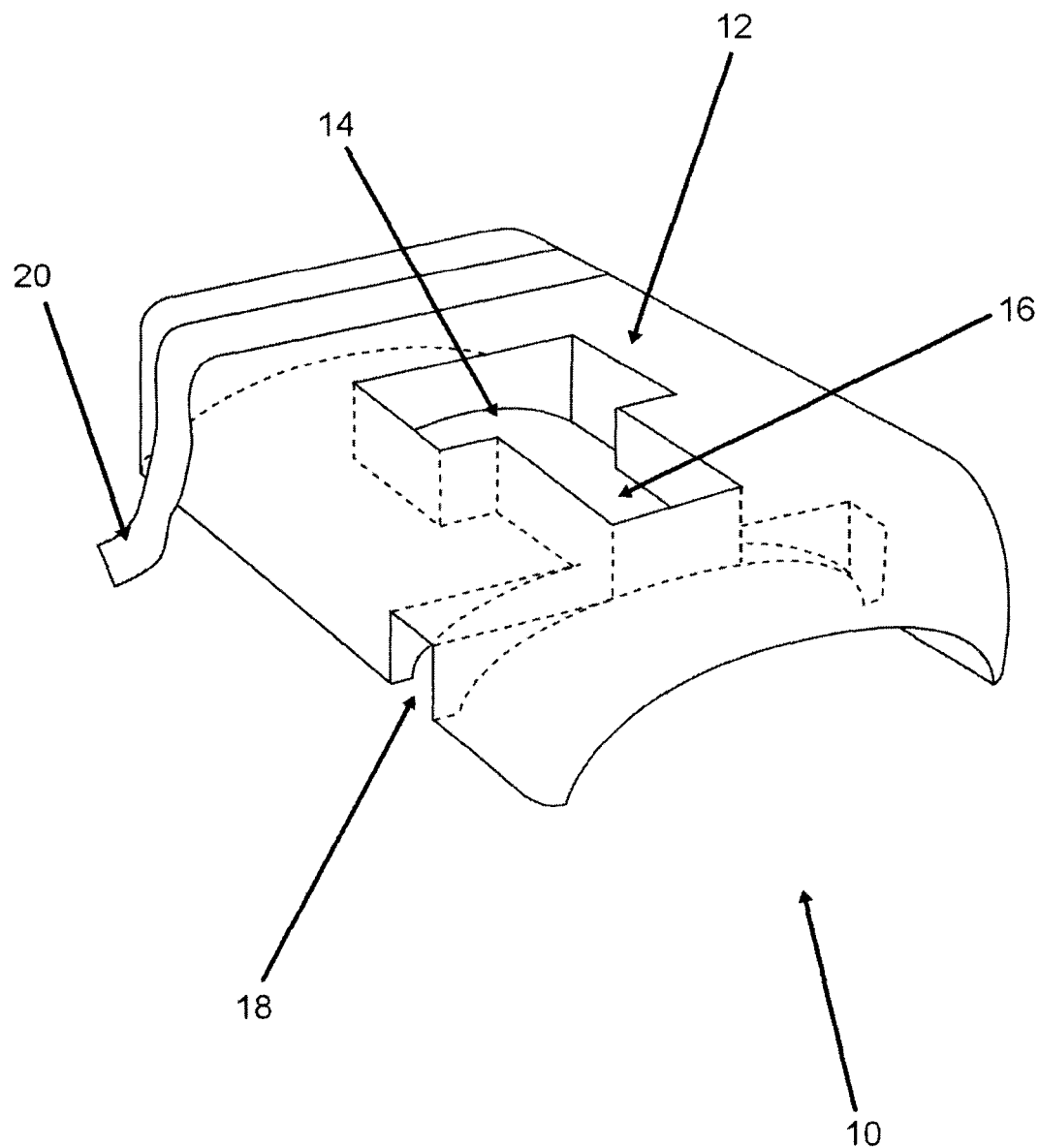
FIG. 11 is a perspective view of the possible embodiment as shown in FIGS. 4-6.

FIG. 11 is a perspective view of the possible embodiment of the face mask 10 as shown in FIGS. 4-6. The face mask 10 comprises the body 12, the opening 14, the opening 16, the notch 18 for an intubation tube, and the strap 20.

Figure 12:
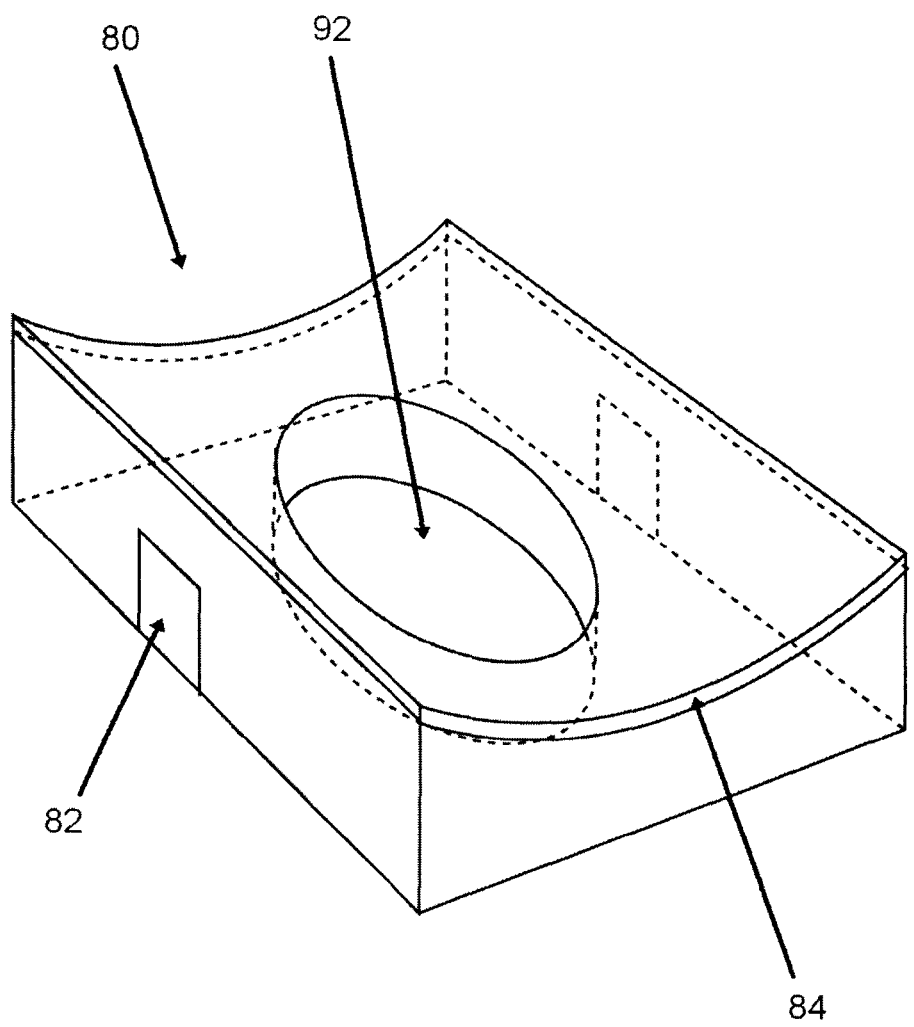
FIG. 12 is a perspective view of the possible embodiment as shown in FIGS. 7-9.

FIG. 12 is a perspective view of the possible embodiment of a head rest 80 as shown in FIGS. 7-9. The head rest 80 comprises the strap receiving members 82. The strap receiving members 82 may comprise a hook and loop arrangement. In other possible embodiments of the present application, the strap receiving members may comprise magnets, snaps, adhesives, or other fixing mechanisms. The head rest 80 also comprises the viscoelastic foam layer 84 and the hollowed out area 92.

Figure 12A:
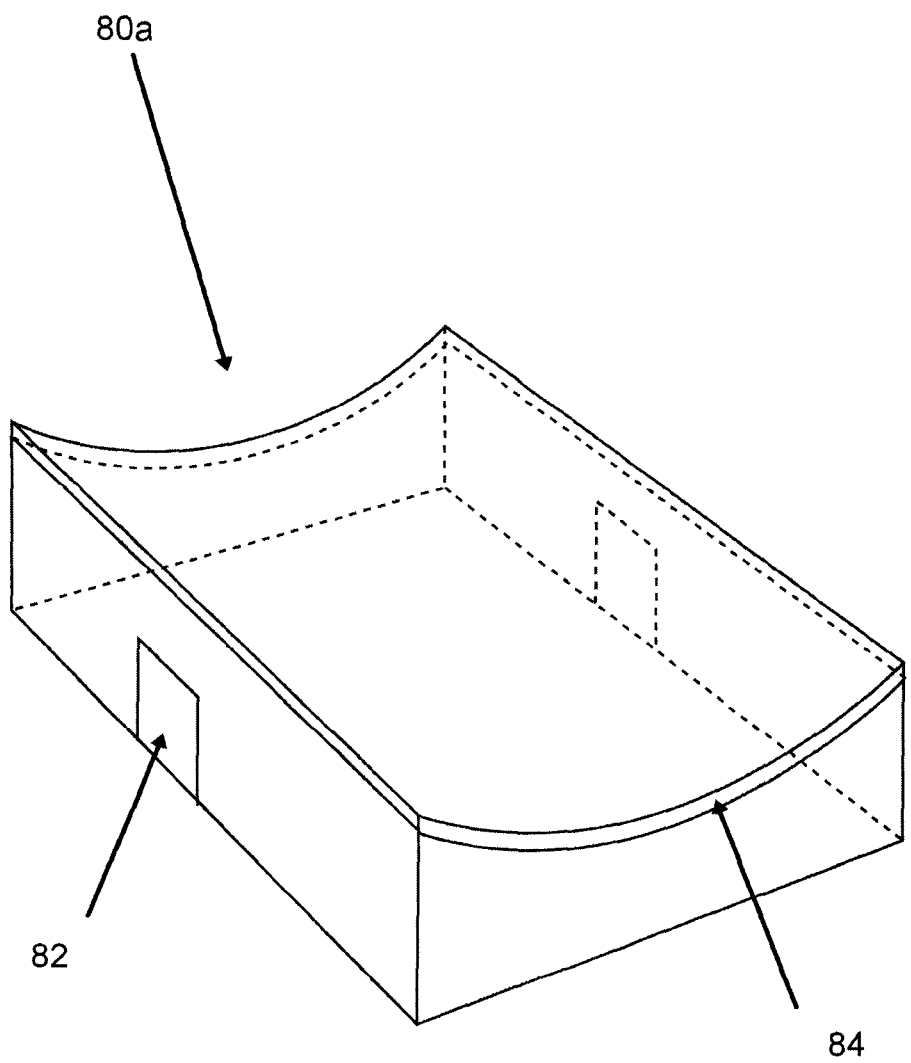
FIG. 12A shows a perspective view of another possible embodiment of a head rest 80a according to the present application.

FIG. 12A shows a perspective view of another possible embodiment of a head rest 80a according to the present application. The head rest 80a does not comprise any hollowed out areas. The head rest 80a comprises strap receiving members 82 and the viscoelastic foam layer 84.

Figure 13:
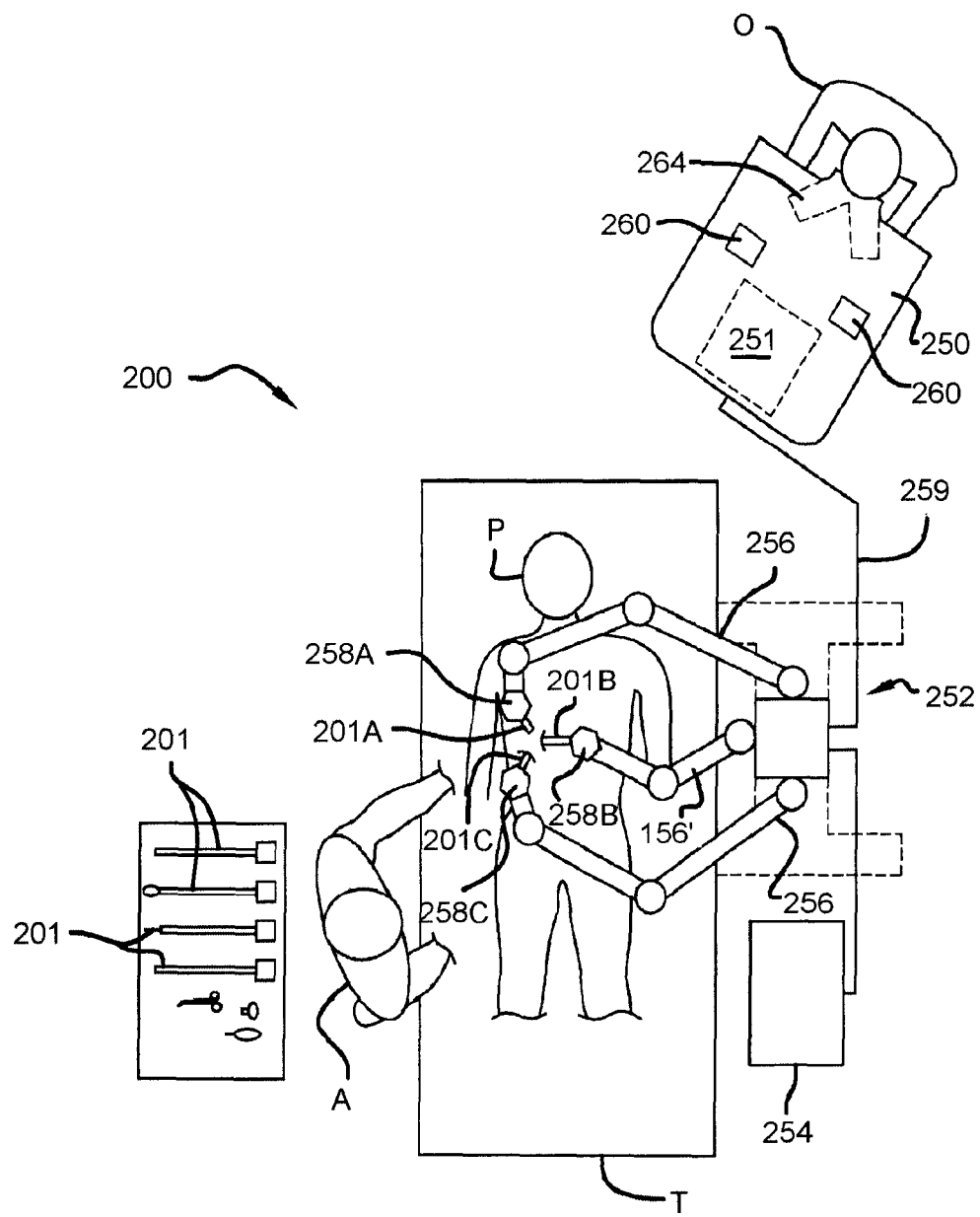
FIG. 13 is a block diagram of a robotic surgery system to perform minimally invasive robotic surgical procedures using one or more robotic surgical arms with a strap drive train.

Referring now to FIG. 13, a block diagram of a robotic surgery system 200 is illustrated to perform minimally invasive robotic surgical procedures using one or more robotic arms with strap drive. Robotic surgery generally involves the use of a robot manipulator that has multiple robotic manipulator arms. One or more of the robotic manipulator arms often support a surgical tool which may be articulated (such as jaws, scissors, graspers, needle holders, micro dissectors, staple appliers, tackers, suction/irrigation tools, clip appliers, or the like) or non-articulated (such as cutting blades, cautery probes, irrigators, catheters, suction orifices, or the like). At least one of the robotic manipulator arms (e.g., the center robotic manipulator arm 258B) is used to support a stereo or three dimensional surgical image capture device 210 such as a stereo endoscope (which may be any of a variety of structures such as a stereo laparoscope, arthroscope, hysteroscope, or the like), or, optionally, some other stereo imaging modality (such as ultrasound, fluoroscopy, magnetic resonance imaging, or the like). Robotic surgery may be used to perform a wide variety of surgical procedures, including but not limited to open surgery, neurosurgical procedures (such as stereotaxy), endoscopic procedures (such as laparoscopy, arthroscopy, thoracoscopy), and the like.

A user or operator O (generally a surgeon) performs a minimally invasive surgical procedure on patient P by manipulating control input devices 260 at a master control console 250. A computer 251 of the console 250 directs movement of robotically controlled endoscopic surgical instruments 201A-201C by means of one or more control cables 259, effecting movement of the instruments using a robotic patient-side system 252 (also referred to as a patient-side cart). The robotic patient-side system 252 has one or more robotic arms 258. In one possible embodiment of the Da Vinci Surgical System, the one or more robotic arms 258 have a strap drive system. Typically, the robotic patient-side system 252 includes at least three robotic manipulator arms 258A-258C supported by linkages 256, 256', with a central robotic arm 258B supporting an endoscopic camera 201B and the robotic arms 258A, 258C to left and right of center supporting tissue manipulation tools 201A and 201C.

Generally, the robotic patient-side system 252 includes a positioning portion and a driven portion. The positioning portion of the robotic patient-side system 252 remains in a fixed configuration during surgery while manipulating tissue. The driven portion of the robotic patient-side system 252 is actively articulated under the direction of the operator O generating control signals at the surgeon's console 250 during surgery. The actively driven portion of the robotic patient-side system 252 is generally referred to herein as the robotic arms or alternatively to robotic surgical manipulators. The positioning portion of the robotic patient-side system 252 that is in a fixed configuration during surgery may be referred to as "set up arms" 256, 256' with positioning linkage and/or "set-up joints" (SUJ). In an alternate embodiment of the Da Vinci Surgical System, the robotic patient-side system 252 may be replaced by set up arms that couple at one end to left and right sides of the operating table T. The three robotic manipulator arms 258A-258C may then be coupled to the opposite end of the set-up arms to ground to the table T.

For convenience in terminology, manipulators such as robotic surgical arms 258A and 258C actuating the tissue affecting surgical tools 201A and 201C are generally referred to herein as a PSM (patient-side manipulators), and a robotic surgical arm 258B controlling an image capture or data acquisition device, such as the endoscopic camera 201B, is generally referred to herein as a ECM (endoscope-camera manipulator), it being noted that such telesurgical robotic manipulators may optionally actuate, maneuver and control a wide variety of instruments, tools and devices useful in surgery. The surgical tools 201A, 201C and endoscopic camera 201B may be generally referred to herein as tools or instruments 201.

An assistant A may assist in pre-positioning of the robotic patient-side system 252 relative to patient P as well as swapping tools or instruments 201 for alternative tool structures, and the like, while viewing the internal surgical site via an assistant's display 254. With the embodiments of the Da Vinci Surgical System, the assistant A may also swap in and out the robotic surgical arms 258A and 258C, as well as the robotic surgical arm 258B, in case one is defective or failing. In other cases, a robotic surgical arm may be swapped out for maintenance, adjustments, or cleaning and then swapped back in by one or more service persons.

Figure 14:
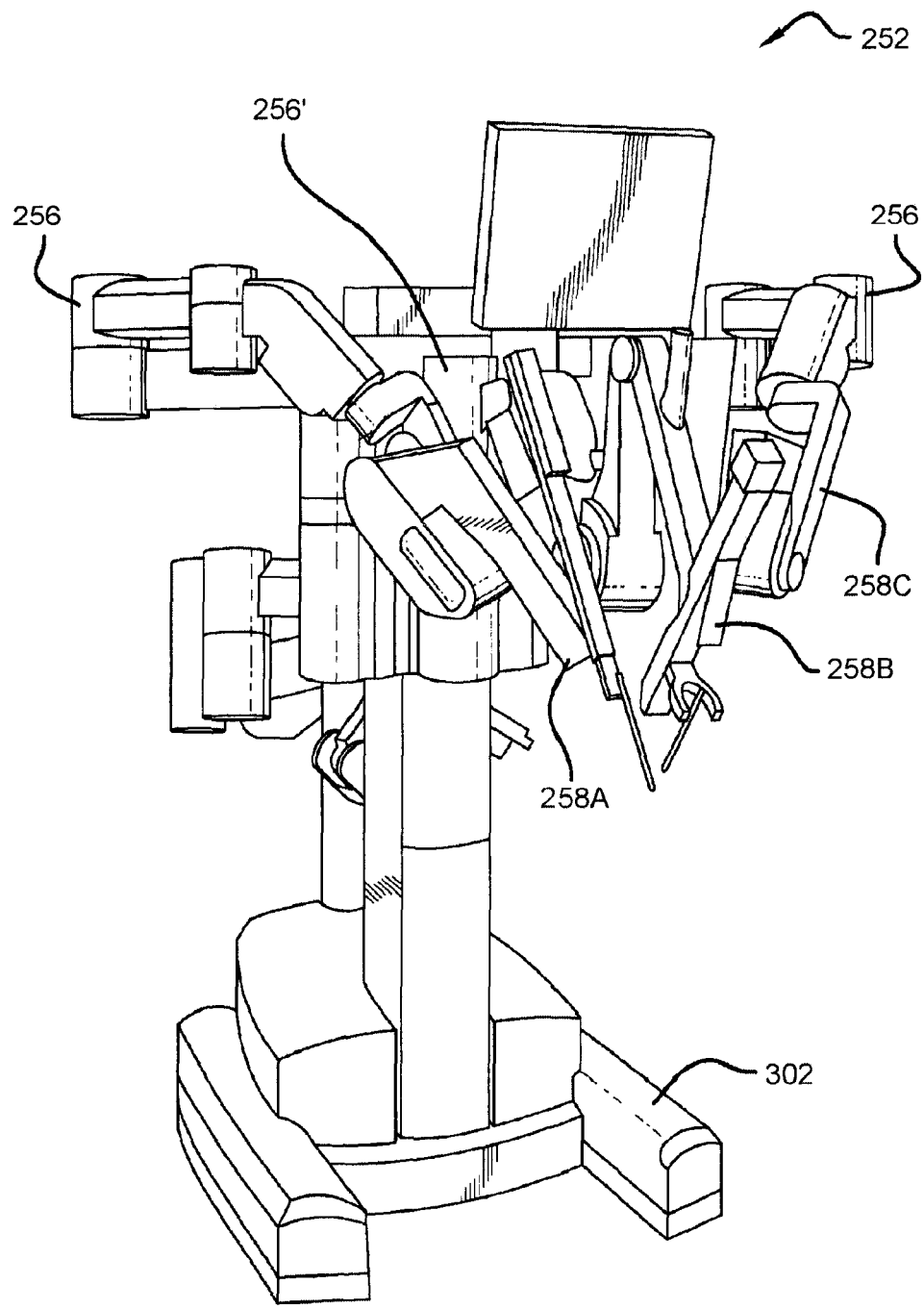
FIG. 14 a perspective view of the robotic patient-side system of FIG. 13 with the one or more robotic surgical arms having the strap drive train.

Referring now to FIG. 14, a perspective view of the robotic patient-side system 252 is illustrated. The robotic patient-side system 252 may have one or more robotic surgical arms (a.k.a., robotic surgical manipulators) 258A-258C with a strap drive system. The robotic arms 258A, 258C are for coupling to robotic surgical tools 201A, 201C. The robotic arm 258B is for coupling to an endoscopic camera 201B. Generally, the surgical robotic arms 258A-258C may be referred to as a surgical robotic arm or a robotic surgical arm 258.

The robotic patient-side system 252 further includes a base 302 from which the robotic surgical instruments 201 may be supported. In at least one possible embodiment of the Da Vinci Surgical System, the robotic surgical instruments 201 are each supported by the positioning linkage 256 and the surgical robotic arms 258. The linkage structures may optionally be covered by protective covers or not to minimize the inertia that is manipulated by the servomechanism and the overall weight of robotic patient-side system 252.

The robotic patient-side system 252 generally has dimensions suitable for transporting between operating rooms. It typically can fit through standard operating room doors and onto standard hospital elevators. The robotic patient-side system 252 may have a weight and a wheel (or other transportation) system that allows the cart to be positioned adjacent to an operating table by a single attendant. The robotic patient-side system 252 may be sufficiently stable during transport to avoid tipping and to easily withstand overturning moments that may be imposed at the ends of the robotic arms during use.

Figure 15:
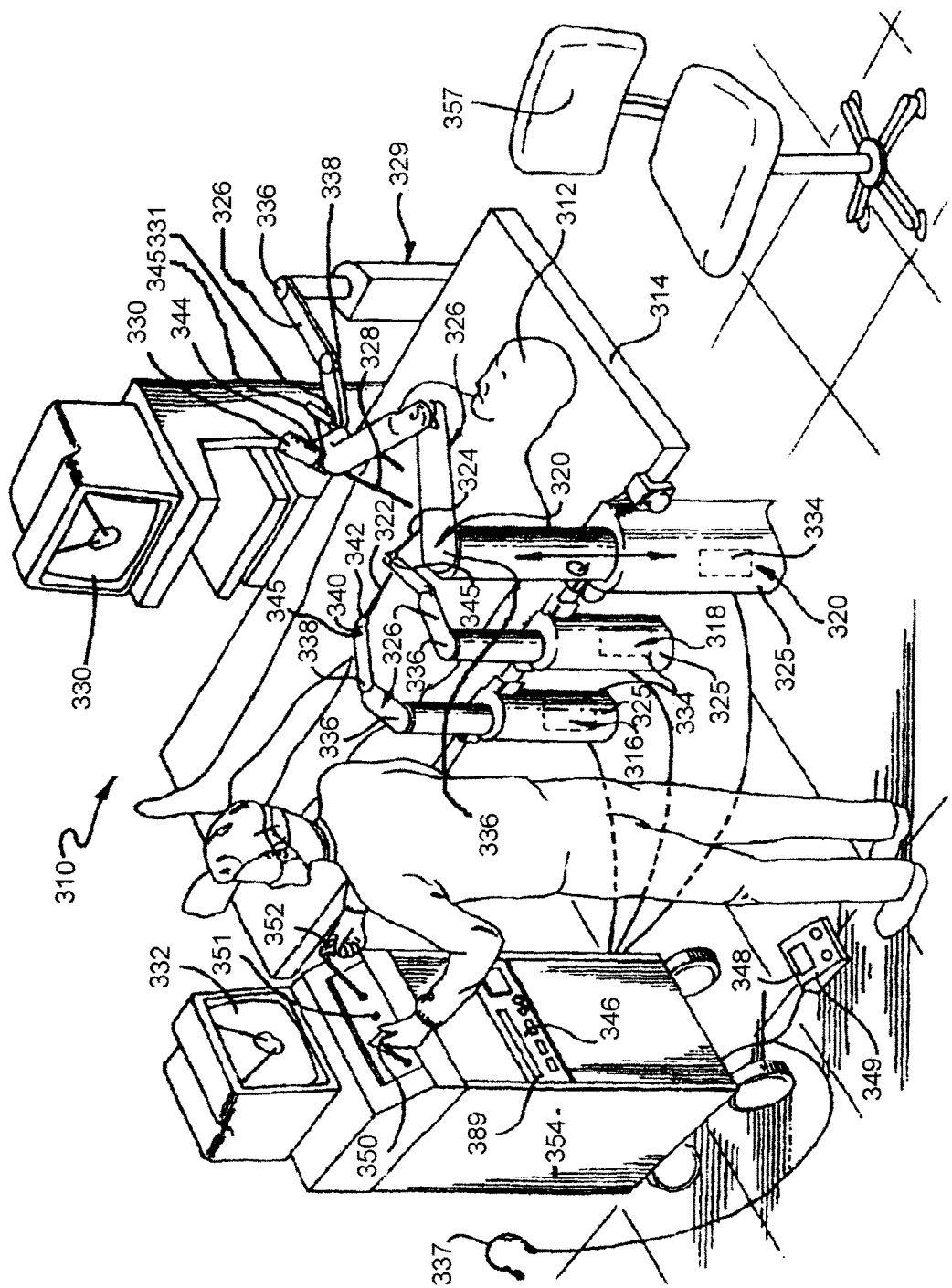
FIG. 15 shows an example of robotic surgery.

FIG. 15 shows an example of a robotic surgery system 310, in which at least one possible embodiment of the Trendelenburg pad could be utilized. In robotic surgery, the consistency of location of the patient is paramount because a shift in position may interfere with the relative positioning of the instruments used in surgery. Due to the ability of the Trendelenburg pad to hold or assist in holding a patient in a desired position, the Trendelenburg pad could be used in robotic surgery. The system 10 may be used to perform a procedure on a patient 312 that is typically lying on an operating table 314. Mounted to the operating table 314 is a first articulate arm 316, a second articulate arm 318 and a third articulate arm 320. The articulate arms 316-320 are mounted to the table so that the arms are in a plane proximate the patient.

The articulate arms 316, 318 and 320 may each comprise a base housing 325 and a robotic arm assembly 326 extending from the base housing 325. Surgical instruments 322 and 324 may be removably coupled at the end of each robotic arm assembly 326 of the first and second articulate arms 316, 318. Each of the instruments 322, 324 may be coupled to a corresponding robotic arm assembly 326.

The third articulate arm 320 may additionally comprise a base housing 325 and a robotic arm assembly 326, and has a first endoscope 328 that is attached to the robotic arm assembly 326. The base housing 325 and robotic arm assemblies 326 of each of the articulate arms 316, 318, and 320 are substantially similar. Additionally, a fourth robotic arm 329 may be included in the system 310. The fourth arm 329 may hold a second endoscope 331.

The instruments 322, 324 and endoscope 328 may be inserted through incisions cut into and through the skin of the patient 312. The first endoscope 328 may comprise a camera 330 that may be coupled to a monitor 332. The monitor 332 may be configured to display images of the internal organs of the patient 312. Additionally, the second endoscope 331 may be inserted through a corresponding incision made in the patient's skin. The second endoscope 331 may be used to provide a wide field of view as depicted in FIG. 15. The second endoscope 331 may be mounted to the fourth robotic arm 329 and may be coupled to a second monitor 333.

Each robotic arm assembly 326 may comprise a base motor 334 which moves the arm assembly 326 in a linear fashion, relative to the base housing 325, as indicated by arrow Q. Each robotic arm assembly 326 may also comprise a first rotary motor 336 and a second rotary motor 338. Each of the robotic arm assemblies 326 may also comprise a pair of passive joints 340 and 342. The passive joints 340, 342 may be disposed orthogonal to each other to provide pivotal movement of the instruments 322, 324 or the endoscopes 328, 331 attached to a corresponding robotic arm assembly 326. The joint angle may be controlled to a particular value using a feedback control loop. The robotic arm assemblies 326 may also comprise a coupling mechanism 345 to couple the instruments 322 and 324, or endoscope 328, 331 thereto. Additionally, each of the robotic arm assemblies 326 may comprise a motor driven worm gear 344 being configured to rotate the instrument 322, 324 or endoscope 328, 331 attached thereto about its longitudinal axis.

The first, second, and third articulate arms 316, 318, 320, as well as the fourth arm 329, may be coupled to a controller 346 which may control the movement of the arms. The arms may be coupled to the controller 346 via wiring, cabling, or via a transmitter/receiver system such that control signals may be passed from the controller 346 to each of the articulate. Each arm 316, 318, 320 and 329 may be electrically connected to the controller 346 via electrical cabling 347.

The controller 346 may be connected to an input device 348 such as a foot pedal, hand controller, or voice recognition unit, to control the position of the endoscope 328 or the second endoscope. To effectuate voice recognition, a microphone 337 is included in the system 310. The controller 346 receives the input signals from the input device 348 and moves the endoscope 328 and robotic arm assembly 326 of the third articulate arm 320 in accordance with the input commands of the surgeon.

The movement and positioning of instruments 322, 324 attached to the first and second articulate arms 316 and 318 is controlled by a surgeon at a pair of master handles 350 and 352. Additionally, a switch 351 may be included in the system 310. The switch 351 may be used by the surgeon to allow positioning of the fourth arm 329. The handles 350 and 352 may be mounted to a portable cabinet 354. A television monitor 356 may be placed onto the cabinet 354 and coupled to the endoscope 328 so that the surgeon can readily view the internal organs of the patient 312. To accommodate a seated position, a chair 357 may be provided with the system.

Figure 16:
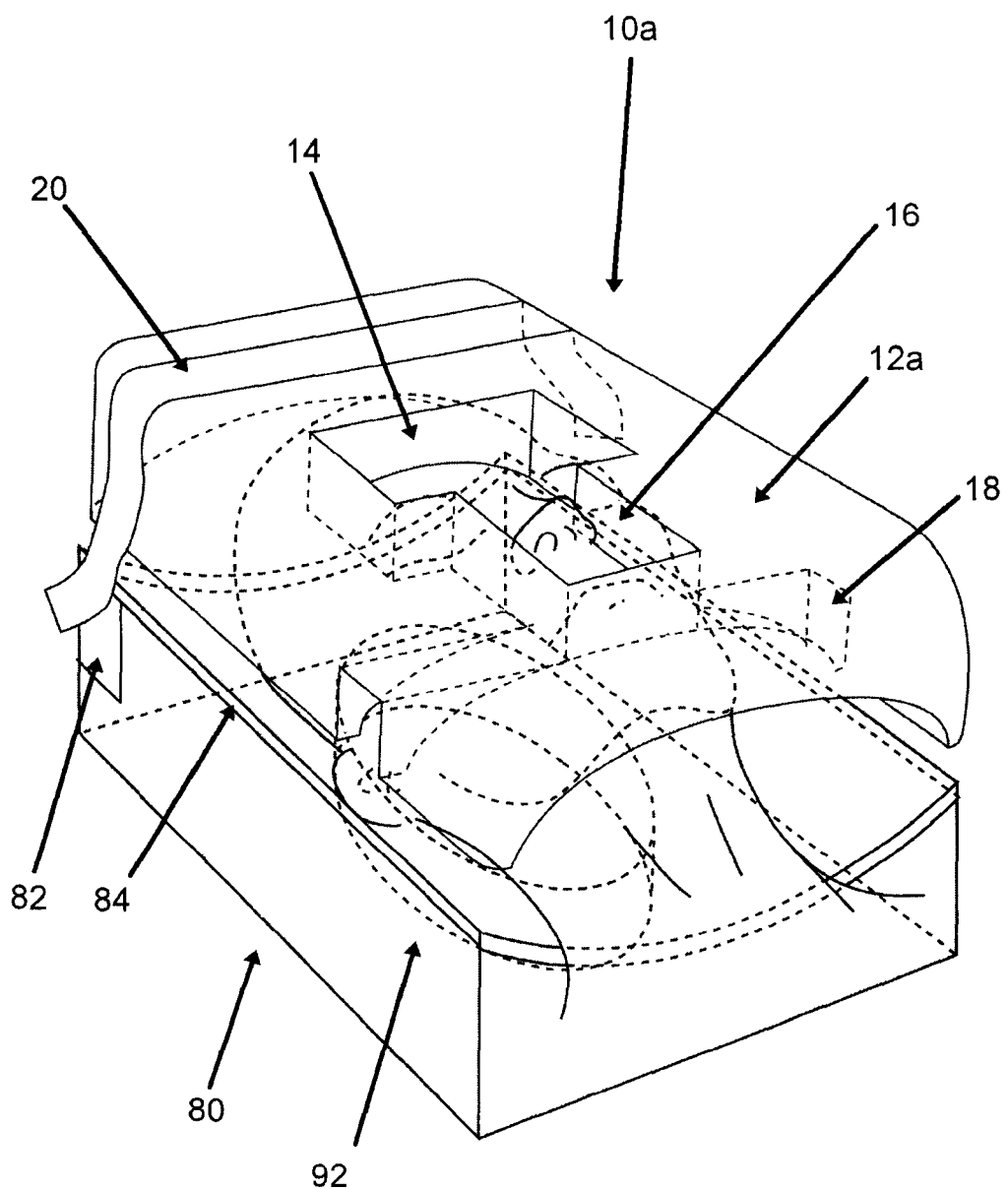
FIG. 16 shows one possible embodiment of the patient protection system of the present application in use with a patient's head disposed in the patient protection system.

FIG. 16 shows one possible embodiment of the patient protection system in use, comprising the face mask 10a and the head rest 80. FIG. 16 shows the patient protection system for exemplary purposes. In one possible embodiment of the present application, the face mask 10a and the head rest 80 may not touch during use. In another possible embodiment of the present application, the face mask 10a and the head rest 80 may touch during use. The face mask 10a comprises the body 12a, the opening 14, the opening 16, the intubation tube notch 18, and strap 20. The head rest 80 comprises the strap receiving member 82, the viscoelastic foam layer 84, and the hollowed out area 92. The strap 20 of the face mask 10a is configured to attach to the strap receiving member 82 to hold the face mask 10a in place over a patient's head. The strap 20 and the strap receiving member 82 may comprise hook and loop arrangements, magnets, snaps, adhesives, or other attaching mechanisms.

Figure 17:
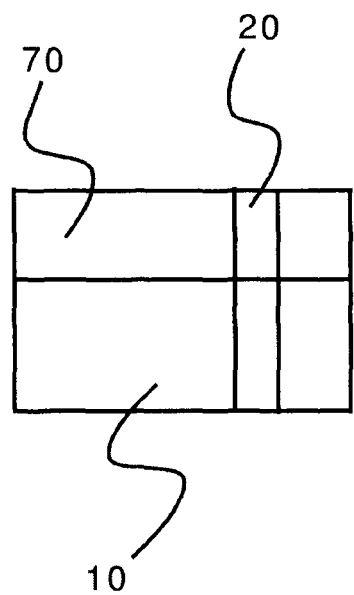
FIG. 17 is a diagram of another possible embodiment of the patient protection system of the present application for use during robotic surgery or a medical procedure, for example, such as back surgery.

FIG. 17 is a diagram of another possible embodiment of the patient protection system of the present application for use during robotic surgery or a medical procedure, for example, such as back surgery. The face mask portion 10 of the patient protection system is disposed below the head portion 70, so that the patient can lie in the prone position, i.e. face down, with the patient's face in the face mask portion 10 and the back of the head portion 70 disposed above and on top of the back of the patient's head. The back of the head portion 70 may comprise a hard plastic covering to protect the back of the patient's head from robotic instruments. The strap 20 is configured and disposed to attach the back of the head portion 70 to the face mask 10.

The viscoelastic foam of the present application may be a polyurethane foam made by mixing polyhydroxy polyol with toluene di-isocyanate or other and different methods as are known in the art. For example, Toluene di-isocyanate may be used in combination with polyester polyols and polyether to make viscoelastic foam.

The headrest and face mask of the present application can be used in conjunction with the METHOD OF SECURING A PATIENT ONTO AN OPERATING TABLE WHEN THE PATIENT IS IN THE TRENDELENBURG POSITION AND APPARATUS THEREFOR INCLUDING A KIT, U.S. Pat. No. 8,464,720, U.S. patent application Ser. No. 13/737,552, filed on Jan. 9, 2013, having inventors Alessio PIGAZZI and Glenn KEILAR, and U.S. Pat. No. 8,511,314, U.S. patent application Ser. No. 13/773,290, filed on Feb. 21, 2013, having inventors Alessio PIGAZZI and Glenn KEILAR.

One feature or aspect of an embodiment is believed at the time of the filing of this patent application to possibly reside broadly in a method of protecting a patient on a medical procedure table during a robotic operation, said method comprising use of a robotic patient protection system comprising a head mask structure configured to protect the head of a patient for use in robotic surgical procedures, said mask structure comprising: a face covering polyethylene foam body configured to substantially conform to the face of the patient; said face covering polyethylene body being covered by a hard plastic covering membrane, configured to be disposed away from the face of the patient, covering the outer surface of said polyethylene foam body; a viscoelastic open cell foam disposed on the inner portion of said body which is configured to be disposed toward the patient's face; a headrest member configured to hold the back of the head of the patient during an operation which headrest member comprises a hollowed out portion configured to receive the back of the head of the patient; a strap member attaching arrangement with a hook or loop strap connected to said hard portion of said outer surface of said mask; a hook or loop member connected to said headrest member and configured to attach to said strap member hook or loop attaching arrangement; said face covering polyethylene body covered with said hard plastic covering providing a safety covering for the head of the patient in the event of a malfunction by either the surgeon or the software thereby preventing or substantially preventing or minimizing injury to the patient upon a portion of the robotic surgical apparatus striking the hard plastic covered body; putting the back of the head of the patient in the headrest; placing said face covering polyethylene foam body with the hard covering and the viscoelastic layer on the patient and connecting the straps to the headrest; and preventing or substantially preventing or minimizing injury to the patient upon a portion of the robotic surgical apparatus striking the hard plastic cover body.

Another feature or aspect of an embodiment is believed at the time of the filing of this patent application to possibly reside broadly in a method of protecting a patient on a medical procedure table during a robotic operation, said method comprising use of a head mask structure configured to protect the head of a patient, said mask structure comprising: a face covering foam body configured to substantially conform to the face of the patient; said face covering body being covered by a hard plastic covering configured to be disposed away from the face of the patient covering the outer surface of said foam body; a soft face-conforming material disposed on the inner portion of said face covering body which soft face-conforming material is disposed and configured to be disposed toward the patient's face; a headrest member configured to hold the back of the head of the patient during an operation which headrest member comprises a hollowed out portion configured to receive the back of the head of the patient; strap member attaching arrangement connected to one of: said hard portion of said outer surface of said mask; and said headrest member; a connecting member connected to said headrest member and configured to attach to said strap member hook or loop attaching arrangement; said face covering body covered with said hard plastic covering providing a safety covering for the head of the patient in the event of a malfunction by either the surgeon or the software thereby said safety covering preventing or substantially preventing or minimizing injury to the patient upon a portion of the robotic surgical apparatus striking the hard plastic covering said face covering body; said method comprising the steps of: putting a portion of the head of the patient in the headrest; placing said face covering foam body with the hard covering on the patient and connecting the attachment arrangement to the headrest; and preventing or substantially preventing or minimizing injury to the patient upon a portion of the robotic surgical apparatus striking the hard plastic cover body.

Yet another feature or aspect of an embodiment is believed at the time of the filing of this patent application to possibly reside broadly in a method of protecting a patient on a medical procedure table during a robotic operation, said method comprising use of a head mask structure configured to protect the head of a patient, said mask structure comprising: a first head covering body part configured to substantially conform to the face of the patient; said first head covering body part being covered by a hard plastic covering configured to be disposed away from the face of the patient covering the outer surface of said first head covering body part; a soft face-conforming material disposed on the inner portion of said first head covering body part which soft face-conforming material is disposed and configured to be disposed toward the patient's face; a second head covering body part configured to hold the back of the head of the patient during an operation which second head covering body part comprises a hollowed out portion configured to receive the back of the head of the patient; a part attaching arrangement connected to one of: said hard portion of said first head covering body part; and said second head covering body part; a connecting member connected to said second head covering body part and configured to attach to said part attaching arrangement; said first head covering body part covered with said hard plastic covering providing a safety covering for the head of the patient in the event of a malfunction by either the surgeon or the software thereby said safety covering preventing or substantially preventing or minimizing injury to the patient upon a portion of the robotic surgical apparatus striking the hard plastic covering said first head covering body part; said method comprising the steps of: putting a portion of the head of a patient in said first head covering body part; putting a portion of the head of the patient in said second head covering body part; aligning said first head covering body part with the hard covering on the patient and connecting the part attachment arrangement to said second head covering body part; and preventing or substantially preventing or minimizing injury to the patient upon a portion of the robotic surgical apparatus striking the hard plastic cover body.

Still another feature or aspect of an embodiment is believed at the time of the filing of this patent application to possibly reside broadly in the method of protecting a patient on a medical procedure table during a robotic operation, said method comprising use of a head mask structure configured to protect the head of a patient, wherein said mask structure further comprises: said first connecting member attaching arrangement is configured to be connected to said first head covering body part; and said second connecting member attaching arrangement is configured to be connected to said second head covering body part.

A further feature or aspect of an embodiment is believed at the time of the filing of this patent application to possibly reside broadly in the method of protecting a patient on a medical procedure table during a robotic operation, said method comprising use of a head mask structure configured to protect the head of a patient, wherein said mask structure further comprises a head-conforming material disposed on at least one of: the inner portion of said first head covering body part and said second head covering body part which is configured to be disposed toward the patient's face and configured to be substantially matchable to the patient's face.

Another feature or aspect of an embodiment is believed at the time of the filing of this patent application to possibly reside broadly in the method of protecting a patient on a medical procedure table during a robotic operation, said method comprising use of a head mask structure configured to protect the head of a patient, wherein said head-conforming material is sufficiently soft to conform to the patient's head and is configured to be disposed toward the patient's head and configured to be substantially matchable to the patient's head.

Yet another feature or aspect of an embodiment is believed at the time of the filing of this patent application to possibly reside broadly in the method of protecting a patient on a medical procedure table during a robotic operation, said method comprising use of a head mask structure configured to protect the head of a patient, wherein said head-conforming material comprises a viscoelastic material being sufficiently soft to conform to the patient's face and is configured to be disposed toward the patient's head and configured to be disposed toward the patient's head and configured to be substantially matchable to the patient's head.

Still another feature or aspect of an embodiment is believed at the time of the filing of this patent application to possibly reside broadly in the method of protecting a patient on a medical procedure table during a robotic operation, said method comprising use of a head mask structure configured to protect the head of a patient, wherein said viscoelastic material comprises an open cell foam.

A further feature or aspect of an embodiment is believed at the time of the filing of this patent application to possibly reside broadly in the method of protecting a patient on a medical procedure table during a robotic operation, said method comprising use of a head mask structure configured to protect the head of a patient, wherein said second head covering body part is configured to hold the back of the head of the patient during a medical procedure, which second head covering body part comprises a hollowed out portion configured to receive the back of the head of the patient.

Another feature or aspect of an embodiment is believed at the time of the filing of this patent application to possibly reside broadly in the method of protecting a patient on a medical procedure table during a robotic operation, said method comprising use of a head mask structure configured to protect the head of a patient, wherein said first connecting member attaching arrangement comprises a strap, which strap comprises a hook or loop arrangement configured to be connected to said hard covering of said head mask structure.

Yet another feature or aspect of an embodiment is believed at the time of the filing of this patent application to possibly reside broadly in a head protecting mask configured to protect a patient on a medical procedure table during a robotic medical procedure, which head protecting mask is configured for use according to the method, said head protecting mask comprising: a head covering body comprising a first part and a second part, said first head covering body part comprising a hollowed out portion configured to receive a portion configured to receive a portion of the head of a patient; said first head covering body part being configured to be disposed above said second head covering body part during use and being covered by a hard covering, configured to be disposed away from the head of the patient, covering the outer surface of said first head covering body part; said second head covering body part being configured to hold a portion of the head of the patient during a medical procedure, which second head covering body part comprises a hollowed out portion configured to receive a portion of the head of the patient; a first connecting member attaching arrangement connected to one of: said first head covering body part; and said second head covering body part; a second connecting member attachment arrangement connected to the other of: said first head covering body part; and said second head covering body part; said first head covering body part covered with said hard covering being configured to be disposed to provide a safety covering for the head of the patient in the event of a malfunction, such as, by either the surgeon or the software, wherein said hard covering is configured to prevent or substantially prevent or minimize injury to the patient upon a portion of the robotic surgical apparatus striking the hard covering of said head covering body.

Still another feature or aspect of an embodiment is believed at the time of the filing of this patent application to possibly reside broadly in the head protecting mask configured to protect a patient on a medical procedure table during a robotic medical procedure, which head protecting mask is configured for use according to the method, wherein: said first connecting member attaching arrangement is configured to be connected to said first head covering body part; and said second connecting member attaching arrangement is configured to be connected to said second head covering body part.

A further feature or aspect of an embodiment is believed at the time of the filing of this patent application to possibly reside broadly in the head protecting mask configured to protect a patient on a medical procedure table during a robotic medical procedure, which head protecting mask is configured for use according to the method, wherein said head protecting mask further comprises a head-conforming material disposed on at least one of: the inner portion of said first head covering body part and said second head covering body part which is configured to be disposed toward the patient's head and configured to be substantially matchable to the patient's head.

One feature or aspect of an embodiment is believed at the time of the filing of this patent application to possibly reside broadly in the head protecting mask configured to protect a patient on a medical procedure table during a robotic medical procedure, which head protecting mask is configured for use according to the method, wherein said head protecting mask further comprises a head-conforming material disposed on at least one of: the inner portion of said first head covering body part and said second head covering body part which is configured to be disposed toward the patient's face and configured to be substantially matchable to the patient's face.

Another feature or aspect of an embodiment is believed at the time of the filing of this patent application to possibly reside broadly in the head protecting mask configured to protect a patient on a medical procedure table during a robotic medical procedure, which head protecting mask is configured for use according to the method, wherein said head-conforming material is sufficiently soft to conform to the patient's head and is configured to be disposed toward the patient's head and configured to be substantially matchable to the patient's head.

Yet another feature or aspect of an embodiment is believed at the time of the filing of this patent application to possibly reside broadly in the head protecting mask configured to protect a patient on a medical procedure table during a robotic medical procedure, which head protecting mask is configured for use according to the method, wherein said head-conforming material comprises a viscoelastic material being sufficiently soft to conform to the patient's face and is configured to be disposed toward the patient's head and configured to be substantially matchable to the patient's head.

Still another feature or aspect of an embodiment is believed at the time of the filing of this patent application to possibly reside broadly in the head protecting mask configured to protect a patient on a medical procedure table during a robotic medical procedure, which head protecting mask is configured for use according to the method, wherein said viscoelastic material comprises an open cell foam.

A further feature or aspect of an embodiment is believed at the time of the filing of this patent application to possibly reside broadly in the head protecting mask configured to protect a patient on a medical procedure table during a robotic medical procedure, which head protecting mask is configured for use according to the method, wherein said second head covering body part is configured to hold the back of the head of the patient during a medical procedure, which second head covering body part comprises a hollowed out portion configured to receive the back of the head of the patient.

Another feature or aspect of an embodiment is believed at the time of the filing of this patent application to possibly reside broadly in the head protecting mask configured to protect a patient on a medical procedure table during a robotic medical procedure, which head protecting mask is configured for use according to the method, wherein said first connecting member attaching arrangement comprises a strap, which strap comprises a hook or loop arrangement configured to be connected to said hard covering of said head protecting mask.

Yet another feature or aspect of an embodiment is believed at the time of the filing of this patent application to possibly reside broadly in the head protecting mask configured to protect a patient on a medical procedure table during a robotic medical procedure, which head protecting mask is configured for use according to the method, wherein said second connecting member attachment arrangement connected to said second head covering body part.

The components disclosed in the patents, patent applications, patent publications, and other documents disclosed or incorporated by reference herein, may possibly be used in possible embodiments of the present invention, as well as equivalents thereof.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

The appended drawings in their entirety, including all dimensions, proportions and/or shapes in at least one embodiment of the invention, are accurate and are hereby included by reference into this specification.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

All, or substantially all, of the components and methods of the various embodiments may be used with at least one embodiment or all of the embodiments, if more than one embodiment is described herein.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

All of the patents, patent applications, patent publications, and other documents cited herein, and in the Declaration attached hereto, are hereby incorporated by reference as if set forth in their entirety herein except for the exceptions indicated herein.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

It will be understood that the examples of patents, patent applications, patent publications, and other documents which are included in this application and which are referred to in paragraphs which state "Some examples of . . . which may possibly be used in at least one possible embodiment of the present application . . . " may possibly not be used or useable in any one or more embodiments of the application.

The sentence immediately above relates to patents, patent applications, patent publications, and other documents either incorporated by reference or not incorporated by reference.

U.S. Provisional Patent Application No. 61/793,874, filed on Mar. 15, 2013, and title "ROBOTIC PATIENT PROTECTION SYSTEM", is hereby incorporated by reference as if set forth in its entirety herein, except for the exceptions indicated herein.

U.S. provisional patent application 61/654,339, filed on Jun. 1, 2012, and title "METHOD OF SECURING A PATIENT ONTO AN OPERATING TABLE WHEN THE PATIENT IS IN THE TRENDELENBURG POSITION AND APPARATUS THEREFOR", is hereby incorporated by reference as if set forth in its entirety herein, except for the exceptions indicated herein.

U.S. patent application Ser. No. 13/737,552, filed on Jan. 9, 2013, having inventors Alessio PIGAZZI and Glenn KEILAR, and title "METHOD OF SECURING A PATIENT ONTO AN OPERATING TABLE WHEN THE PATIENT IS IN THE TRENDELENBURG POSITION AND APPARATUS THEREFOR INCLUDING A KIT", is hereby incorporated by reference as if set forth in its entirety herein, except for the exceptions indicated herein.

U.S. patent application Ser. No. 13/773,290, filed on Feb. 21, 2013, having inventors Alessio PIGAZZI and Glenn KEILAR, and title "METHOD OF SECURING A PATIENT ONTO AN OPERATING TABLE WHEN THE PATIENT IS IN THE TRENDELENBURG POSITION AND APPARATUS THEREFOR INCLUDING A KIT", is hereby incorporated by reference as if set forth in its entirety herein, except for the exceptions indicated herein.

International patent application PCT/US2013/020824, filed on Jan. 9, 2013, having inventors Alessio PIGAZZI and Glenn KEILAR, and title "METHOD OF SECURING A PATIENT ONTO AN OPERATING TABLE WHEN THE PATIENT IS IN THE TRENDELENBURG POSITION AND APPARATUS THEREFOR INCLUDING A KIT", is hereby incorporated by reference as if set forth in its entirety herein, except for the exceptions indicated herein.

An example of a robotic surgery system, such as the Da Vinci Surgical System, is made by Intuitive Surgical, Inc., located at 1266 Kifer Road #101, Sunnyvale, Calif. 94086.

U.S. Pat. No. 8,066,524, having the title "SURGICAL SYSTEM WITH ELECTRO-MECHANICAL INTERFACES TO MOUNT ROBOTIC SURGICAL ARMS," issued on Nov. 29, 2011, is hereby incorporated by reference as if set forth in its entirety herein except for the exceptions indicated herein.

Kevlar® is a registered trademark of for a para-aramid synthetic fiber registered to DuPont, headquartered at 1007 Market Street, Wilmington, Del. 19898, USA. Some examples of Kevlar® may be which may possibly be utilized in at least one possible embodiment of the present application, may possibly be found in the following U.S. Pat. No. 8,302,213, having the title "Helmets and vests," issued on Nov. 6, 2012; and U.S. Pat. No. 4,574,105, having the title "Penetration resistant textile panels with plies of nylon and plies of Kevlar," issued on Mar. 4, 1986.

Some examples of viscoelastic foam, which may possibly be utilized in at least one possible embodiment of the present application, may possibly be found in the following U.S. Pat. No. 7,078,443, having the title "Viscoelastic foam layer and composition," issued on Jul. 18, 2006; U.S. Pat. No. 8,399,085, having the title "Energy-absorbing pads," issued on Mar. 19, 2013; U.S. Pat. No. 8,359,689, having the title "Mattress adapted for supporting heavy weight persons," issued on Jan. 29, 2013; U.S. Pat. No. 7,789,461, having the title "Seating accessory," issued on Sep. 7, 2010; U.S. Pat. No. 6,895,619, having the title "Foldable pillow," issued on May 24, 2005; and U.S. Pat. No. 6,453,476, having the title "Protective helmet," issued on Sep. 24, 2002.

Some examples of polyethylene foam, which may possibly be utilized in at least one possible embodiment of the present application, may possibly be found in the following U.S. Pat. No. 6,245,266, having the title "Method for making oriented polyethylene foam and foam produced thereby", issued on Jun. 12, 2001; U.S. Pat. No. 5,206,082, having the title "Nondistorted polyethylene foam structures and process for making", issued on Apr. 27, 1993; U.S. Pat. No. 4,877,814, having the title "Process for producing open-cell polyethylene foam materials and the resultant product", issued on Oct. 31, 1989; U.S. Pat. No. 4,719,039, having the title "Electrically conductive polyethylene foam," issued on Jan. 12, 1988; U.S. Pat. No. 4,220,730, having the title "Crosslinked chlorinated polyethylene foam", issued on Sep. 2, 1980; and U.S. Pat. No. 4,209,473, having the title "Crosslinked chlorinated polyethylene foam", issued on Jun. 24, 1980. Some examples of polypropylene foam, which may possibly be utilized in at least one possible embodiment of the present application, may possibly be found in the following U.S. Pat. No. 7,799,841, having the title "Polypropylene foam", issued on Sep. 21, 2010; U.S. Pat. No. 7,759,404, having the title "Inherently open-celled polypropylene foam with large cell size", issued on Jul. 20, 2010; U.S. Pat. No. 6,773,796, having the title "Thermoformable multi-layer polypropylene foam sheet", issued on Aug. 10, 2004; U.S. Pat. No. 5,567,742, having the title "Dimensionally-stable polypropylene foam expanded with inorganic blowing agents", issued on Oct. 22, 1996; U.S. Pat. No. 5,527,573, having the title "Extruded closed-cell polypropylene foam", issued on Jun. 18, 1996; and U.S. Pat. No. 5,180,751, having the title "Polypropylene foam sheets", issued on Jan. 19, 1993.

U.S. provisional patent application 61/793,874, filed on Mar. 15, 2013, having inventor Paul LLOYD, and title "ROBOTIC PATIENT PROTECTION SYSTEM", is hereby incorporated by reference as if set forth in their entirety herein.

All of the references and documents cited in any of the patents, patent applications, patent publications, and other documents cited herein, except for the exceptions indicated herein, are hereby incorporated by reference as if set forth in their entirety herein except for the exceptions indicated herein. All of the patents, patent applications, patent publications, and other documents cited herein, referred to in the immediately preceding sentence, include all of the patents, patent applications, patent publications, and other documents cited anywhere in the present application.

Words relating to the opinions and judgments of the author of all patents, patent applications, patent publications, and other documents cited herein and not directly relating to the technical details of the description of the embodiments therein are not incorporated by reference.

The words all, always, absolutely, consistently, preferably, guarantee, particularly, constantly, ensure, necessarily, immediately, endlessly, avoid, exactly, continually, expediently, ideal, need, must, only, perpetual, precise, perfect, require, requisite, simultaneous, total, unavoidable, and unnecessary, or words substantially equivalent to the above-mentioned words in this sentence, when not used to describe technical features of one or more embodiments of the patents, patent applications, patent publications, and other documents, are not considered to be incorporated by reference herein for any of the patents, patent applications, patent publications, and other documents cited herein.

The description of the embodiment or embodiments is believed, at the time of the filing of this patent application, to adequately describe the embodiment or embodiments of this patent application. However, portions of the description of the embodiment or embodiments may not be completely applicable to the claims as originally filed in this patent application, as amended during prosecution of this patent application, and as ultimately allowed in any patent issuing from this patent application. Therefore, any statements made relating to the embodiment or embodiments are not intended to limit the claims in any manner and should not be interpreted as limiting the claims in any manner.

The details in the patents, patent applications, patent publications, and other documents cited herein may be considered to be incorporable, at applicant's option, into the claims during prosecution as further limitations in the claims to patentably distinguish any amended claims from any applied prior art.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the embodiment or embodiments, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. § 1.72(b). As stated in 37 C.F.R. § 1.72(b):

> A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims.

Therefore, any statements made relating to the abstract are not intended to limit the claims in any manner and should not be interpreted as limiting the claims in any manner.

The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

What is claimed is:

1. A method of protecting a patient on a medical procedure table during a robotic operation, said method comprising use of a head mask structure configured to protect a head of the patient, said head mask structure comprising:
   a first head covering body part configured to substantially conform to a face of the patient, and comprising one or more side notches configured to be aligned with the patient's mouth and configured to allow intubation of the patient;
   said first head covering body part being covered by a hard plastic covering configured to be disposed away from the face of the patient and covering an outer surface of said first head covering body part;
   a soft face-conforming viscoelastic material disposed on an inner portion of said first head covering body part which soft face-conforming viscoelastic material is disposed and configured to be disposed toward the face of the patient;
   a second head covering body part configured to hold a back of the head of the patient during an operation which second head covering body part comprises a hollowed out portion configured to receive the back of the head of the patient;
   a part attaching arrangement connected to one of:
      said hard plastic covering of said first head covering body part; and
      said second head covering body part;
   at least one connecting member connected to said second head covering body part and configured to attach to said part attaching arrangement;
   said first head covering body part covered with said hard plastic covering providing a safety covering for the head of the patient to protect against a malfunction by either a surgeon or a software, said safety covering preventing or substantially preventing or minimizing injury to the patient upon a portion of a robotic surgical apparatus striking the hard plastic covering of said first head covering body part;
   said method comprising the steps of:
      putting a first portion of the head of a patient in said first head covering body part;
      putting the back of the head of the patient in said second head covering body part;
      aligning said first head covering body part with the hard plastic covering on the patient and connecting the part attaching arrangement to said second head covering body part; and
      preventing or substantially preventing or minimizing injury to the patient upon a portion of the robotic surgical apparatus striking the hard plastic covering.

2. The method according to claim 1, wherein said at least one connecting member of said head mask structure further comprises:
   a first connecting member attaching arrangement configured to be connected to said first head covering body part; and
   a second connecting member attaching arrangement configured to be connected to said second head covering body part.

3. The method according to claim 2, wherein soft face-conforming viscoelastic material is disposed on at least one of: the inner portion of said first head covering body part and said second head covering body part which is configured to be disposed toward the face of the patient and configured to be substantially matchable to the face of the patient.

4. The method according to claim 3, wherein said face-conforming viscoelastic material is sufficiently soft to conform to the head of the patient and is configured to be disposed toward the head of the patient and configured to be substantially matchable to the head of the patient.

5. The method according to claim 4, wherein said face-conforming viscoelastic material comprises an open cell foam.

6. The method according to claim 5, wherein said second head covering body part is configured to hold the back of the head of the patient during a medical procedure, which second head covering body part comprises a hollowed out portion configured to receive the back of the head of the patient.

7. The method according to claim 6, wherein said first connecting member attaching arrangement comprises a strap, which strap comprises a hook or loop arrangement configured to be connected to said hard plastic covering of said head mask structure.

8. A head protecting mask configured to protect a patient on a medical procedure table during a robotic medical procedure, said head protecting mask comprising:
   a head covering body comprising a first part and a second part, said first part of the head covering body comprising a hollowed out portion configured to receive a first portion of a head of a patient, and one or more side notches configured to be aligned with the patient's mouth and configured to allow intubation of the patient;
   said first part of the head covering body being configured to be disposed above said second part of the head covering body during use and being covered by a hard covering, configured to be disposed away from the head of the patient, covering an outer surface of said first part of the head covering body;
   said second part of the head covering body being configured to hold a second portion of the head of the patient during the medical procedure, said second part of the head covering body comprising a hollowed out portion configured to receive the second portion of the head of the patient;
   a first connecting member attaching arrangement connected to one of:
      said first part of the head covering body; and
      said second part of the head covering body;
   a second connecting member attachment arrangement connected to the other of:
      said first part of the head covering body; and
      said second part of the head covering body;
   said first part of the head covering body covered with said hard covering being configured to be disposed to provide a safety covering for the head of the patient to protect against a malfunction, wherein said hard covering is configured to prevent or substantially prevent or minimize injury to the patient upon a portion of a robotic surgical apparatus striking the hard covering of said head covering body; and
   a head-conforming viscoelastic material disposed on at least one of: an inner portion of said first part of the head covering body and said second part of the head covering body which is configured to be disposed toward the head of the patient and configured to be substantially matchable to the head of the patient.

9. The head protecting mask according to claim 8, wherein said head-conforming viscoelastic material comprises an open cell foam.

10. The head protecting mask according to claim 9, wherein said second part of the head covering body is configured to hold a back of the head of the patient during the medical procedure, which second part of the head covering body comprises a hollowed out portion configured to receive the back of the head of the patient.

11. The head protecting mask according to claim 10, wherein said first connecting member attaching arrangement comprises a strap, which strap comprises a hook or loop arrangement configured to be connected to said hard covering of said head protecting mask.

12. The head protecting mask according to claim 11, wherein said second connecting member attaching arrangement is connected to said second part of the head covering body.

13. The head protecting mask according to claim 8, wherein:
said first connecting member attaching arrangement is configured to be connected to said first part of the head covering body; and
said second connecting member attaching arrangement is configured to be connected to said second part of the head covering body.

14. The head protecting mask according to claim 8, wherein said head-conforming viscoelastic material is sufficiently soft to conform to the head of the patient and is configured to be disposed toward the head of the patient and configured to be substantially matchable to the head of the patient.

15. A method of protecting a patient on a medical procedure table during a robotic operation, said method comprising use of a robotic patient protection system comprising a head mask structure configured to protect a head of the patient for use in robotic surgical procedures, said head mask structure comprising:
a face covering polyethylene foam body configured to substantially conform to a face of the patient;
said face covering polyethylene foam body being covered by a hard plastic covering, configured to be disposed away from the face of the patient, covering an outer surface of said face covering polyethylene foam body, and comprising one or more side notches configured to be aligned with the patient's mouth and configured to allow intubation of the patient;
a viscoelastic open cell foam layer disposed on an inner portion of said face covering polyethylene foam body which is configured to be disposed toward the face of the patient;
a headrest member configured to hold a back of the head of the patient during an operation which headrest member comprises a hollowed out portion configured to receive the back of the head of the patient;
a strap member attaching arrangement with a hook or loop strap connected to said hard plastic covering of said outer surface of said face covering polyethylene foam body;
a hook or loop member connected to said headrest member and configured to attach to said strap member attaching arrangement;
said face covering polyethylene foam body covered with said hard plastic covering providing a safety covering for the head of the patient to protect against a malfunction by either a surgeon or a software thereby preventing or substantially preventing or minimizing injury to the patient upon a portion of a robotic surgical apparatus striking the hard plastic covering;
putting the back of the head of the patient in the headrest member;
placing said face covering polyethylene foam body with the hard plastic covering and the viscoelastic open cell foam layer on the patient and connecting the strap member attaching arrangement to the headrest member; and
preventing or substantially preventing or minimizing injury to the patient upon a portion of the robotic surgical apparatus striking the hard plastic covering.

16. A method of protecting a patient on a medical procedure table during a robotic operation, said method comprising use of a head mask structure configured to protect a head of the patient, said head mask structure comprising:
a face covering foam body configured to substantially conform to a face of the patient, and comprising one or more side notches configured to be aligned with the patient's mouth and configured to allow intubation of the patient;
said face covering foam body being covered by a hard plastic covering configured to be disposed away from the face of the patient and covering an outer surface of said face covering foam body;
a soft face-conforming viscoelastic material disposed on an inner portion of said face covering foam body which soft face-conforming viscoelastic material is disposed and configured to be disposed toward the face of the patient;
a headrest member configured to hold a back of the head of the patient during an operation which headrest member comprises a hollowed out portion configured to receive the back of the head of the patient;
a strap member attaching arrangement connected to one of:
said hard plastic covering of said outer surface of said face covering foam body; and
said headrest member;
a connecting member connected to said headrest member and configured to attach to said strap member attaching arrangement via a hook or loop attaching arrangement;
said face covering foam body covered with said hard plastic covering providing a safety covering for the head of the patient to protect against a malfunction by either a surgeon or a software, said safety covering preventing or substantially preventing or minimizing injury to the patient upon a portion of a robotic surgical apparatus striking the hard plastic covering of said face covering foam body;
said method comprising the steps of:
putting a portion of the head of the patient in the headrest member;
placing said face covering foam body with the hard plastic covering on the patient and connecting the strap member attaching arrangement to the headrest member; and
preventing or substantially preventing or minimizing injury to the patient upon a portion of the robotic surgical apparatus striking the hard plastic covering.

* * * * *